United States Patent
Kraus et al.

(10) Patent No.: US 12,162,044 B2
(45) Date of Patent: *Dec. 10, 2024

(54) VERIFICATION OF CLEANING PROCESSES WITH ELECTRONICALLY READABLE CODED COUPON

(71) Applicant: Ecolab USA Inc., St. Paul, MN (US)

(72) Inventors: Paul R Kraus, Apple Valley, MN (US); Rachel Marie McGinness, Rosemount, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/469,077

(22) Filed: Sep. 18, 2023

(65) Prior Publication Data
US 2024/0009714 A1    Jan. 11, 2024

Related U.S. Application Data

(63) Continuation of application No. 18/053,888, filed on Nov. 9, 2022, now Pat. No. 11,794,216, which is a
(Continued)

(51) Int. Cl.
*B08B 3/04* (2006.01)
*G06K 7/14* (2006.01)
*G06T 7/00* (2017.01)

(52) U.S. Cl.
CPC ............ *B08B 3/04* (2013.01); *G06K 7/1417* (2013.01); *G06T 7/0008* (2013.01)

(58) Field of Classification Search
CPC ........ B08B 3/04; B08B 13/00; G06K 7/1417; G06T 7/0008; A61B 2090/702;
(Continued)

(56) References Cited

U.S. PATENT DOCUMENTS 5,088,144 A    2/1992    Schneider
6,463,940 B1   10/2002   Thomas et al.
(Continued)

FOREIGN PATENT DOCUMENTS

CN    104463059 A    3/2015
CN    105346252 A    2/2016
(Continued)

OTHER PUBLICATIONS

"Create QR Code," Retrieved from http://www.barcode-generator.org/ on Apr. 10, 2018, 9 pp.
(Continued)

*Primary Examiner* — Kristy A Haupt
(74) *Attorney, Agent, or Firm* — Shumaker & Sieffert, P.A.

(57) ABSTRACT

A soil-based coupon having an electronically readable verification code printed thereon is used for verification of soil removal by a cleaning process. The coupon includes a soil overlay covering the verification code. The verification code is at least partially revealed by removal of all or part of the soil overlay during the cleaning process. If the data encoded in the verification code can be correctly decoded after completion of the cleaning process, the cleaning process can be verified. The soil overlay can be designed to match the application. The coupons may be used in a cleaning process verification procedure in which one or more computing devices analyze images of the verification codes to determine whether or not cleaning processes can be verified.

18 Claims, 8 Drawing Sheets

Related U.S. Application Data continuation of application No. 16/599,033, filed on Oct. 10, 2019, now Pat. No. 11,498,099.

(60) Provisional application No. 62/749,453, filed on Oct. 23, 2018.

(58) Field of Classification Search
CPC .......... A61B 90/70; G16H 40/40; A61L 2/07; A61L 2/28; A61L 2202/24; A47L 15/4295; G01N 2021/945
See application file for complete search history.

(56) References Cited

U.S. PATENT DOCUMENTS

| | | | |
|---|---|---|---|
| 6,488,890 | B1 | 12/2002 | Kirckof |
| 7,437,213 | B2 | 10/2008 | Batcher |
| 8,540,156 | B2 | 9/2013 | Nemet et al. |
| 8,807,422 | B2 | 8/2014 | Nemet |
| 9,289,107 | B2 | 3/2016 | Ellingson et al. |
| 9,476,083 | B2 | 10/2016 | Lee et al. |
| 11,498,099 | B2 | 11/2022 | Kraus et al. |
| 11,794,216 | B2 * | 10/2023 | Kraus .................. G06T 7/0008 |
| 2010/0264640 | A1 | 10/2010 | Lane et al. |
| 2010/0328476 | A1 | 12/2010 | Wagner |
| 2017/0175163 | A1 | 6/2017 | Ahimou et al. |
| 2019/0034684 | A1 | 1/2019 | Xiao et al. |

FOREIGN PATENT DOCUMENTS

| | | |
|---|---|---|
| CN | 106127276 A | 11/2016 |
| JP | 2010220970 A | 10/2010 |
| WO | 0145755 A2 | 6/2001 |
| WO | 2007081004 A1 | 7/2007 |

OTHER PUBLICATIONS

"QR Code Generator," Retrieved from https://www.barcodesinc.com/generator/gr/?chl=Serial+%3A+01%0D%0ALot+%3A+OOO&chs=200x200&cht=qr&chld=H%7CO on Apr. 10, 2018, 1 pp.

"Terragene," Terragene.com, Retrieved from https://www.terragene.com.ar/en/ on Apr. 10, 2018, 3 pp.

"Verify All Clean Washer Inidicator Test for Monitoring Cleaning Processes," Steris Corporation, No. M3306EN. Jan. 2018, Rev D., Jan. 2018, 1 pp.

International Preliminary Report on Patentability from International Application No. PCT/US2019/055727, mailed May 6, 2021, 11 pp.

International Search Report and Written Opinion of counterpart International Application No. PCT/US2019/055727, mailed Feb. 10, 2020, 7 pp.

Prosecution History from U.S. Appl. No. 16/599,033, dated Dec. 17, 2019 through Jul. 12, 2022, 39 pp.

Prosecution History from U.S. Appl. No. 18/053,888, dated Mar. 14, 2023 through Jun. 20, 2023, 21 pp.

Response to Communication Pursuant to Rules 161(1) and 162 EPC dated Jun. 1, 2021, from counterpart European Application No. 19081993.7, filed Dec. 7, 2021, 22 pp.

Notice of Intent to Grant and Text Intended to Grant from counterpart European Application No. 19801993.7 dated Apr. 2, 2024, 61 pp.

* cited by examiner

VERIFICATION OF CLEANING PROCESSES WITH ELECTRONICALLY READABLE CODED COUPON

This application is a continuation of U.S. patent application Ser. No. 18/053,888, filed Nov. 9, 2022, which is a continuation of U.S. patent application Ser. No. 16/599,033, filed Oct. 10, 2019, now issued as U.S. Pat. No. 11,498,099, which claims the benefit of U.S. Provisional Application No. 62/749,453, titled, "VERIFICATION OF CLEANING PROCESSES WITH ELECTRONICALLY READABLE CODED COUPON," filed Oct. 23, 2018, each of which is incorporated by reference herein in its entirety.

BACKGROUND

Automated cleaning machines are used in restaurants, healthcare facilities, and other locations to clean, disinfect, and/or sanitize various articles. In a restaurant or food processing facility, automated cleaning machines (e.g., dishmachines) may be used to clean food preparation and eating articles, such as dishware, glassware, pots, pans, utensils, food processing equipment, and other items. In healthcare facilities, for example, automated washer disinfectors may be used to clean and sterilize medical/surgical instrumentation and other medical items.

In general, articles to be cleaned are placed on a rack and provided to a wash chamber of the automated cleaning machine. In the chamber, one or more cleaning products and/or rinse agents are applied to the articles during a cleaning process. The cleaning process may include one or more wash phases and one or more rinse phases. At the end of the cleaning process, the rack is removed from the wash chamber. Water pressure, water quality, concentration of the chemical cleaning agents, temperature, cycle duration and other factors may impact the efficacy of a cleaning process.

SUMMARY

In one example, the disclosure is related to a verification coupon comprising a substrate including at least one verification area; an electronically readable verification code including encoded verification data printed within the verification area; and a soil overlay covering the verification code, the soil overlay removable by a cleaning process within an automated cleaning machine, and wherein the verification code is at least partially revealed by removal of all or part of the soil overlay during the cleaning process.

In some examples, the cleaning process may be verified if the encoded verification data can be correctly decoded after completion of the cleaning process. The soil overlay may include one of a food-based soil or a medical soil. The electronically readable code may include at least one of a Quick Response Code (QR Code), a Data Matrix or other two-dimensional barcode, a Universal Product Code (UPC), an International or European Article Number (EAN), an International Standard Book Number (ISBN), a Shipping Container Code (SCC), a Code-128 barcode, and a Code-39 barcode. The verification coupon may be mounted on a wall inside a wash chamber of the automated cleaning machine during the cleaning process, or positioned on a rack that is placed inside the wash chamber during the cleaning process.

The substrate may further include a reference area, and the verification coupon may further comprise an electronically readable reference code including encoded reference data printed within the reference area, wherein the encoded reference data matches the encoded verification data; and wherein the cleaning process is verified if data decoded from an image of the verification code after completion of the cleaning process matches data decoded from an image of the reference code.

The cleaning process may be verified if data decoded from the image of the verification code after completion of the cleaning process may be reconstructed to match data decoded from an image of the reference code within a specified tolerance.

In another example, the disclosure is directed to a verification system comprising a plurality of verification coupons, each verification coupon including a substrate defining at least one verification area and having an electronically readable verification code printed within the verification area, each verification coupon further including a soil overlay covering the verification code, and wherein verification code is at least partially exposed by removal of all or part of the soil overlay during a cleaning process of an automated cleaning machine; and at least one processor configured to analyze an image of the verification area of at least one of the plurality of verification coupons after completion of the cleaning process, decode the verification code from the image of the verification area, and to generate, for display on a user interface of a user computing device, a notification indicating whether or not the cleaning process has been verified based on the analysis.

The automated cleaning machine may include a dishwasher, washer/decontaminator, a steam sterilizer, an autoclave, an ultrasonic washer, a tunnel washer, or a cart washer. The articles to be cleaned may include food processing, eating, or preparation articles, a surgical instrument or a medical device. The soil overlay may include at least one of a food-based soil, an organic soil, or an inorganic soil.

The system may further include a server computing device remotely located from the user computing device, and wherein the server computing device includes the at least one processor. The user computing device may include the at least one processor.

In another example, the disclosure is directed to a method comprising running a cleaning process in an automated cleaning machine with a verification coupon present in a wash chamber of the automated cleaning machine, the verification coupon including a verification area and having an electronically readable verification code printed within a verification area and a soil overlay covering the verification code, and at least a portion of the verification code is revealed by removal of all or part of the soil overlay during the cleaning process; capturing a digital image of the verification area after completion of the cleaning process; analyzing the image of the verification area to decode the portion of the verification code revealed by removal of all or part of the soil overlay during the cleaning process; and generating, for display on a user interface of a user computing device, a notification indicating whether or not the cleaning process has been verified based on the analysis.

The method may further include verifying the cleaning process if data decoded from the portion of the verification code revealed by removal of all or part of the soil overlay matches data decoded from a reference code. The method may further include generating a notification indicating that the cleaning process passed the verification procedure if data decoded from the portion of the verification code revealed by removal of all or part of the soil overlay matches data decoded from a reference code. The method may further include generating a notification indicating that the cleaning process failed the verification procedure if data decoded from the portion of the verification code revealed by removal of all or part of the soil overlay does not match data decoded from a reference code.

Analyzing the image of the verification area may further include applying a first level of error correction to data decoded from the portion of the verification code revealed by removal of all or part of the soil overlay; and verifying the cleaning process if data decoded from the portion of the verification code revealed by removal of all or part of the soil overlay matches data decoded from a reference code when the first level of error correction is applied.

The method may further include generating a notification, for display on a user computing device, indicating a first failure level for the cleaning process if the data decoded from the portion of the verification code revealed by removal of all or part of the soil overlay does not match data decoded from a reference code when the first level of error correction is applied. The notification may include possible reasons for incomplete removal of the soil overlay or corrective action that may be taken to address the incomplete removal of the soil overlay. The possible reasons for incomplete removal of the soil overlay may include at least one of a mechanical failure, a chemistry failure, or a user error.

The method may further include analyzing the image of the verification area to decode the portion of the verification code revealed by removal of all or part of the soil overlay during the cleaning process and obtain therefrom a serial number uniquely identifying the verification coupon; and determining whether the uniquely identified verification coupon has been used to verify a previous cleaning process based on the serial number.

The method may further include generating, for display on a user computing device, generating, for display on a user interface of the user computing device, a notification indicating that the uniquely identified verification coupon has been used to verify the previous cleaning process if the serial number is associated with the previous cleaning process.

The details of one or more examples are set forth in the accompanying drawings and the description below. Other features will be apparent from the description and drawings, and from the claims.

DETAILED DESCRIPTION

Figure 1A:
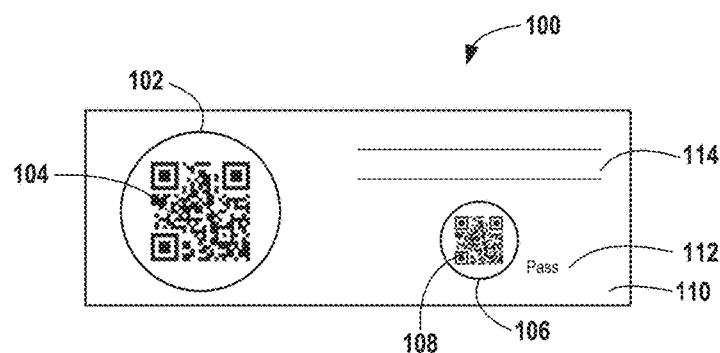
FIG. 1A shows an example electronically readable cleaning process verification coupon in accordance with the present disclosure having an electronically readable code (a QR code) printed thereon.

In accordance with the present disclosure, a cleaning process verification coupon having an electronically readable verification code printed thereon is used for verification of a cleaning process. A soil overlay covers the electronically readable verification code. The verification coupon is subjected to a cleaning process of an automated cleaning machine. At least part of the verification code is revealed by removal of all or part of the soil overlay during the cleaning process. If the data encoded in the verification code can be accurately read after completion of the cleaning process, the cleaning process can be verified, and the cleaning process passes the verification procedure. If the verification code can not be accurately read after completion of the cleaning process, the cleaning process fails the verification procedure. In some examples, the cleaning process verification procedure may be performed on a periodic basis in accordance with a cleaning process verification plan established by a business entity. Verification of the cleaning process can help to ensure proper cleaning, disinfection and/or sterilization of articles to be cleaned.

Each cleaning process verification coupon includes a substrate having an electronically readable verification code printed thereon in a verification area of the substrate. The electronically readable verification code (or simply, "verification code") is covered by a soil overlay. Once subjected to the cleaning process of the automated cleaning machine, if the soil overlay is adequately removed, the cleaning process is verified (e.g., the cleaning process receives a "Pass" score). If the verification code cannot be accurately read following completion of the automated cleaning process, the cleaning process cannot be verified (e.g., the cleaning process receives a "Fail" score).

In other examples, the cleaning process may be quantified in terms of the relative amount of soil removed or remaining as determined by the data read from the electronically readable verification code.

The soil overlay may be designed to match the soil(s) typically encountered for the application. In a healthcare application, for example, the soil overlay may include any type of medical soil(s) (those typically found or representative of those encountered in a medical environment), which may further include organic soils such as protein, lipids, carbohydrates, bone chips, etc., and/or inorganic soils such as saline, simethicone, bone cement, calcium and other minerals, etc. In a restaurant or food processing application, the soil(s) may include any type of food-based soil(s) such as fats and oils, proteins, carbohydrates, dyes, minerals, starches, coffee and tea stains, etc. Other possible soil overlays for these and other applications will be apparent to those of ordinary skill in the art, and the disclosure is not limited in this respect.

The electronically readable code may be any machine-readable representation of data. For example, the electronically readable code may take the form of, but is not limited to, a Quick Response Code (QR Code), a Data Matrix or other two-dimensional barcode, a Universal Product Code (UPC), an International or European Article Number (EAN), an International Standard Book Number (ISBN), a Shipping Container Code (SCC), a Code-128 barcode, a Code-39 barcode, or any other electronically readable code or indicia.

The verification coupon also includes a reference area having an electronically readable reference code (or simply, "reference code") printed within the reference area. The reference code is not covered by a soil overlay. The reference code is identical to (e.g., contains the same data as) the verification code. The reference code allows for a comparison (validation) of the data obtained by scanning the verification code or portion of the code exposed by removal of the soil overlay and the data that should be received if the soil overlay is completely or adequately removed. Alternatively or in addition, a comparison of the data obtained from reading the verification code after completion of the cleaning process with the data obtained from reading the reference code may be correlated to an amount or percentage of soil removed or remaining.

The cleaning process verification coupon may be placed at any appropriate location or orientation within the washing environment of the cleaning machine so as to experience a representative cleaning process within the machine. For example, the verification coupon may be positioned where it will be exposed to the same cleaning process experience as articles to be cleaned would experience. If the verification coupon is run through the cleaning process during the same cleaning cycle as articles to be cleaned, the verification coupon may be positioned where it will not block or inhibit flow of cleaning solution, water, steam, air, heat, or other cleaning component circulated throughout the wash chamber, nor inhibit operation of the cleaning machine.

The data codified or encoded in the electronically readable verification code (and thus also in the reference code) may include, for example, soil type, production date, coupon serial number, use-by date, lot numbers, files, maps, Uniform Resource Locator(s) (URLs), image files, or any other information or data that may be relevant or helpful with respect to the cleaning verification procedure.

During a verification procedure, a verification coupon, including the soil overlay, is placed inside the wash chamber of a cleaning machine, such as on or in a rack, on or in an article to be cleaned, mounted to a sidewall within the cleaning machine, etc., and subjected to the cleaning process within the cleaning machine. The verification coupon is cleaned by the combination of the chemistry (active cleaning ingredients) in the cleaning solution and any mechanical action (such as impingement onto or flow of the cleaning solution over the verification coupon) taking place within the cleaning machine. Other factors that may affect the efficacy of the cleaning process include the duration of the cleaning process, including the relative duration of each step or cycle within the overall cleaning process; water and/or air temperature(s) throughout the cleaning process; adherence to defined procedures concerning operation of the cleaning machine; proper mechanical operation of the cleaning machine; etc.

After completion of the cleaning process, the verification coupon is removed from the wash chamber of the cleaning machine. Removal of all or part of the soil overlay reveals at least a portion of the verification code printed onto the substrate of the verification coupon within the verification area.

In some examples, to verify efficacy of the cleaning process, the soil overlay should be adequately removed after completion of the cleaning process. To determine whether or not the soil overlay was adequately removed, a computing device or code reader scans the verification area of the verification coupon after completion of the cleaning process. At least a portion of the verification code will be revealed by removal of all or part of the soil overlay as a result of the cleaning process. In some examples, if the data encoded in the verification code is can be accurately read or decoded (e.g., the data obtained from the verification code is successfully read by the reading device as compared to the data obtained from the reference code) the washing process may be verified. The cleaning process may receive a "Pass" score for the verification procedure). If the verification code is not readable, the washing process cannot be verified, and the cleaning process may receive a "Fail" score for the verification procedure).

In some examples, the data encoded in the electronically readable verification code may be partially or incompletely read by the code reader due to residue from the soil overlay that was not completely removed during the cleaning process, or the code may be unreadable. The amount and content of the data accurately obtained from a verification code may indicate how much of the soil overlay was removed during cleaning, indicate how much of the soil overlay remained after cleaning, identify possible reasons for incomplete removal of the soil overlay (i.e., possible causes of the failure to adequately remove the soil overlay, such as a mechanical related failure or a chemistry related failure), and/or identify corrective action that may be taken to address the incomplete removal of the soil overlay. The amount and content of the data accurately obtained from a verification code may further be correlated to a cleaning score. The cleaning score may be indicative of how much soil was removed or remains after completion of the cleaning process, possible reasons for the incomplete soil removal, and/or corrective action that may be taken to address the incomplete removal of the soil overlay.

Figure 1B:
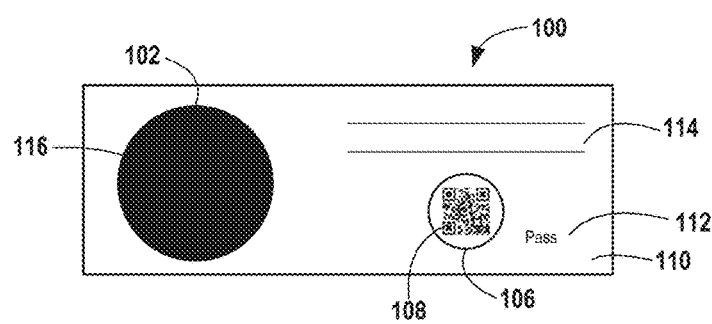
FIG. 1B shows the QR code covered with a representative tenacious soil.

FIG. 1A shows an example electronically readable cleaning process verification coupon 100 having an electronically readable verification code (a QR code in this example) 104 printed thereon. FIG. 1B shows verification coupon 100 with a representative soil overlay 116 that covers verification code 104. Verification coupon 100 includes a substrate 110 having a verification area 102 and a reference area 106. Verification code 104 is located within verification area 102. Soil overlay is also located within the verification area and covers verification code 104. An electronically readable reference code 108 is located within reference area 106. Verification coupon 100 also includes an optional "Pass" text indicia next to reference area 106. This communicates to a user that verification code 106 is the code to read for purposes of comparison. A writable area 114 allows a user to add identification information or other notes to the coupon. The identification information may include, for example, the date and time of the cleaning cycle, identification of the cleaning machine, identification of the person running the cleaning cycle and/or the verification procedure, a "pass" or "fail" indication, and/or other information relevant to the cleaning process verification procedure. The verification coupon 100 may further include a printed serial number uniquely identifying the particular coupon and visually readable by a human being, or electronically readable by a computing device. In addition, or alternatively, the unique serial number may be encoded in the verification and references codes 104 and 108.

In this example, verification code 104 and reference code 108 are identical in the sense that they include the same electronically readable printed pattern and thus contain the same data encoded therein. Verification code 104 is initially under the soil overlay 116 before being subjected to a cleaning process and may therefore be considered a "challenge code", in that the readability of the verification code 104 after completion of the cleaning process is an indication of the efficacy of the cleaning process when subjected to the challenge of removing the soil overlay. Reference code 108 may considered a "validation code" in that the data obtained from reading the verification code 104 after completion of the cleaning process may be compared to the data read from reference code 108 to determine the amount and content of data accurately obtained from verification code 104 and thus the completeness (or incompleteness) of removal of the soil overlay by the cleaning process.

Figure 2A:
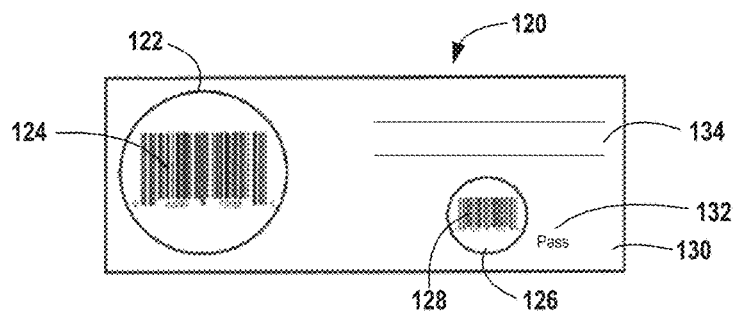
FIG. 2A shows another example electronically readable cleaning process verification coupon in accordance with the present disclosure having an electronically readable code (a barcode or UPC) printed thereon.
Figure 2B:
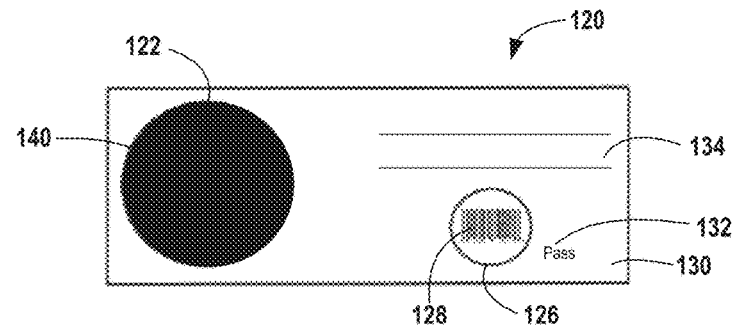
FIG. 2B shows the barcode covered with a representative tenacious soil.

FIG. 2A shows another example electronically readable cleaning process verification coupon 120 having an electronically readable verification code (in this example a UPC or barcode) 124 printed thereon. FIG. 2B shows verification coupon 120 having a representative soil overlay 140 that covers verification code 124. Verification coupon 120 includes a substrate 130 having a verification area 122 and a reference area 126. Verification code 124 is located within verification area 122. Soil overlay 140 is located within verification area 122 and over verification code 124. Reference code 128 is located within reference area 126. Verification coupon 120 also includes a "Pass" text indication 132 next to second verification area 126. A writable area 134 allows a user to add identification information or other notes to the coupon as described above with respect to FIGS. 1A and 1B.

It shall be understood that the electronically readable verification and/or reference code(s) used with the cleaning verification techniques described herein may include any machine-readable representation of data or indicia, and that the disclosure is not limited in this respect. For example, the electronically readable code(s) may take the form of, but are not limited to, a Quick Response Code (QR Code), a Data Matrix or other two-dimensional barcode, a Universal Product Code (UPC), an International or European Article Number (EAN), an International Standard Book Number (ISBN), a Shipping Container Code (SCC), a Code-128 barcode, a Code-39 barcode, or any other electronically readable code or indicia.

Substrate 110/130 may include a temperature stable material onto which electronically readable verification and reference codes and other indicia may be printed and onto which the soil overlay may be printed or transferred. Examples of suitable substrate materials include, but are not limited to polyethylene, polypropylene, polyester, polyvinyl chloride (vinyl), high density polyethylene (HDPE), synthetic forms of paper, plastics, ceramics, and metals.

In some examples, the data encoded in the verification code (and the reference code) includes a unique coupon identifier, such as serial number. Once a verification coupon is read, the serial number may be uploaded from a local computing device, such as the device used to scan the verification and/or reference code(s), to a remote computing device, such as a local or remote computing device or a cloud-based server computer. Upon receiving the verification coupon serial number, the remote computing device may analyze the serial number to determine whether the specific coupon has been used to verify a previous cleaning process. This may help to prevent fraudulent re-use of a verification coupon in order to falsify cleaning process verification results.

Figure 3:
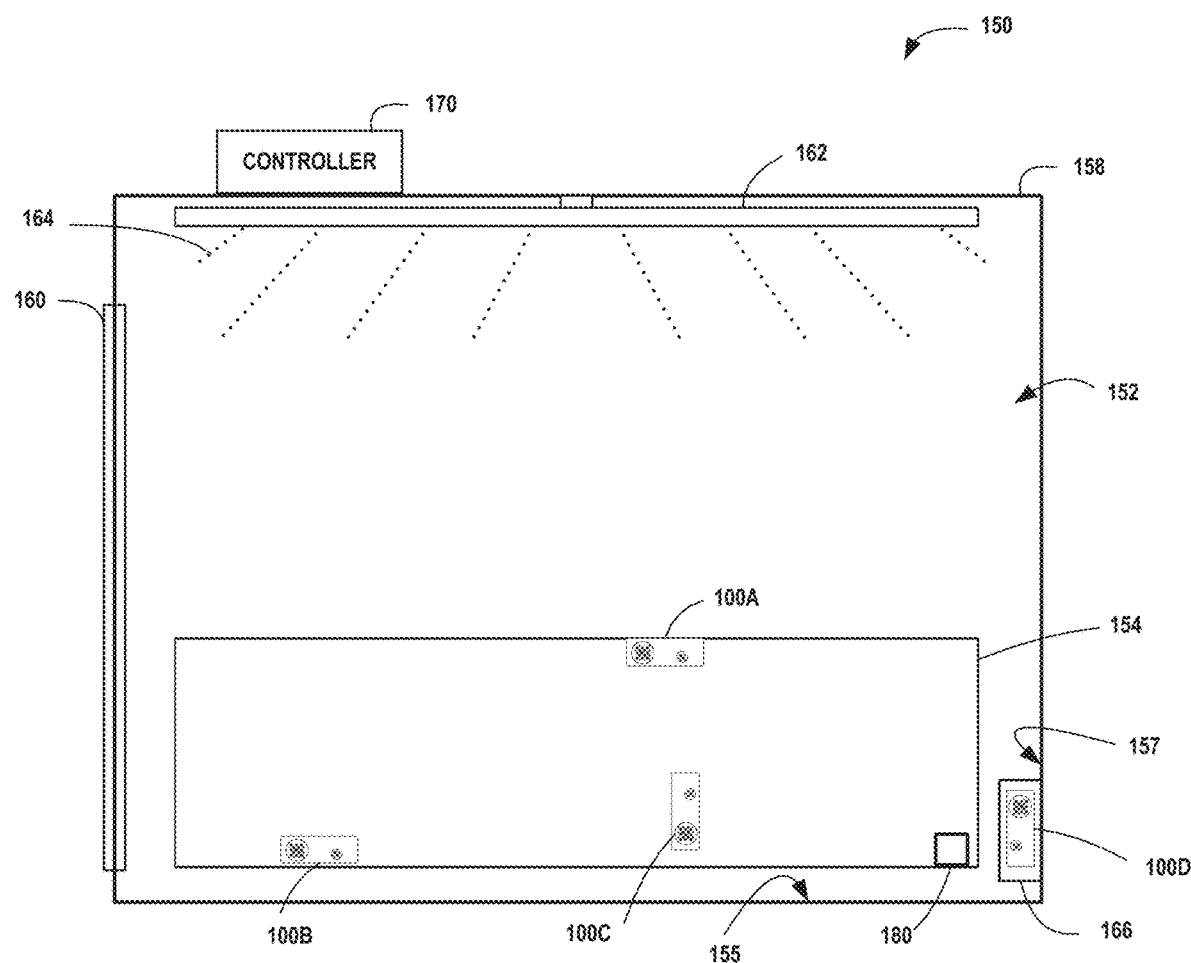
FIG. 3 shows an example automated cleaning machine in which one or more electronically readable cleaning process verification coupons may be used to verify a cleaning process in accordance with the present disclosure.

FIG. 3 shows an example automated cleaning machine 150 in which one or more electronically readable cleaning process verification coupons 100 may be used to verify a cleaning process in accordance with the present disclosure. In this example, cleaning machine 150 is a dishmachine for cleaning eating and/or food preparation articles including one or more of pots and pans, dishware, glassware, eating and cooking utensils, etc. It shall be understood, however, that cleaning machine 150 may include any other type of cleaning machine such as clothes or textile washing machines, medical instrument reprocessors, automated washer disinfectors, autoclaves, sterilizers, or any other type of cleaning machine, and that the disclosure is not limited in this respect.

Cleaning machine 150 includes an enclosure 158 defining one or more wash chamber(s) 152 and having one or more door(s) 160 that permit entry and/or exit into wash chamber 152. One or more removable rack(s) 154 are sized to fit inside wash chamber 152. Each rack 154 may be configured to receive articles to be cleaned directly thereon, or they may be configured to receive one or more trays or holders into which articles to be cleaned are held during the cleaning process. The racks 154 may be general or special-purpose racks, and may be configured to hold large and/or small items, food processing/preparation equipment such as pots, pans, cooking utensils, etc., and/or glassware, dishes and other eating utensils, etc. In a hospital or healthcare application, the racks may be configured to hold instrument trays, hardgoods, medical devices, tubing, masks, basins, bowls, bed pans, or other medical items. It shall be understood that the configuration of racks 154, and the description of the items that may be placed on or in racks 154, as shown and described with respect to FIG. 1 and throughout this specification, are for example purposes only, and that the disclosure is not limited in this respect.

A typical cleaning machine such as cleaning machine 150 operates by spraying one or more cleaning solution(s) 164 (a mixture of water and one or more chemical cleaning products) into wash chamber 152 and thus onto the articles to be cleaned. The cleaning solution(s) are pumped to one or more spray arms 162, which spray the cleaning solution(s) 164 into wash chamber 152 at the appropriate times. Cleaning machine 150 is provided with a source of fresh water and, depending upon the application, may also include one or more sumps to hold used wash and/or rinse solution to be reused in the next cleaning cycle. Cleaning machine 150 may also include or be provided with a chemical product dispenser that automatically dispenses the appropriate chemical product(s) at the appropriate time(s) during the cleaning process, mixes them with the diluent, and pumps the resulting cleaning solution(s) 164 into the wash chamber 152. Depending upon the machine, the articles to be cleaned, the amount of soil on the articles to be cleaned, and other factors, one or more wash cycles may be interspersed with one or more rinse and/or sanitization cycles to form one complete cleaning process of cleaning machine 150.

Automated cleaning machine 150 further includes a controller 170. Controller 170 includes one or more processor(s) that monitor and control various parameters of the cleaning machine 150 such as cycle time(s) and length(s), cleaning solution concentrations, timing for and amounts of chemical product dispensed, water temperature(s), heated air temperature(s), wash chamber temperature(s), humidity, application of water and chemical products into the wash chamber, etc.

As shown in FIG. 3, one or more cleaning process verification coupon(s), such as verification coupon(s) 100A-100D, may be placed in various locations within the wash chamber 152 or on or in rack(s) 154 during a cleaning process. In this example, verification coupons 100A-100C are located in or on rack 154. Coupon 100D is located in a mounting bracket or holder 166 affixed to a sidewall 157 of wash chamber 152. Placing multiple verification coupons, such as coupons 100A-100D, in different areas of the wash chamber 152 as shown in FIG. 3 may help to verify a complete and effective cleaning process throughout the entire wash chamber 152. In other examples, a single verification coupon 100 may be used for each a cleaning cycle. The number of verification coupons used per cleaning cycle may depend upon the type of articles to be cleaned, the type of cleaning machine, the type(s) of soil to be removed, and/or the cleaning process and verification procedures defined by the enterprise or business entity, among other things. It shall be understood, therefore, that the number of verification coupons used per cleaning cycle is not limited in this respect.

The walls 155, 157 of wash chamber 152 and/or racks 154 may further include a verification coupon mounting bracket, holder, clip, or other fastener, such as coupon holder 166, configured to support a verification coupon during a cleaning process. In some examples, the holder, clip or other fastener may be manually attached to or placed in a rack 154 or one or more walls of the wash chamber 152 prior to the start of a cleaning process. In other examples, the holder, clip or fastener may be molded directly into one or more walls of the wash chamber 152, or molded directly onto a rack 154. In that example, the verification coupon would be placed into the molded holder prior to the start of the cleaning process. In other examples, the fastener or holder may include a screw, a push-in plastic rod, a circular protrusion that would fit into a hole in a rack or tray, a rib that would snap in to a matching slot feature on a rack or tray, or by using a clip modified either during molding of the rack or the rack may need to be retrofitted. It shall be understood that the coupon holder may be any of suitable type, and that the disclosure is not limited in this respect.

In some examples, the coupon holder is designed to simulate a realistic challenge to the cleaning process of the types of articles to be cleaned. For example, items such as certain types of cooking equipment, utensils, medical devices or surgical instrumentation may include harder to reach areas that are more difficult to thoroughly clean during a cleaning process. To that end, the coupon holder may include walls having one or more screens, apertures, or slots that at least partially obscure the soil overlay portion of a verification coupon to provide a more realistic challenge to the cleaning process.

Verification coupons 100 may be placed at any location within the wash chamber 152, and may be located in position(s) where they do not interfere with the spray of the cleaning solution(s) and/or mechanical operation of cleaning machine 150. Verification coupons 100 may further be of an appropriate size so as not block spray of the cleaning solution during the cleaning process or interfere with mechanical operation of cleaning machine 150.

In some examples, verification coupons 100 are rectangular in shape and have overall dimensions (length and width) of sufficient size to accommodate suitably sized electronically readable verification and reference codes. That is, the electronically readable codes should be large enough to be recognized and read by the code reader application under typical cleaning process verification conditions. For example, a smart phone QR code reader application may have a relationship between the scan distance and the minimum QR code size of approximately Thus, if a verification coupon will typically be scanned using a QR code reader on a smart phone at a scanning distance between 6 and 12 inches, the QR codes (verification and reference codes) may be at least approximately 0.6 inches to 1.2 inches square. The overall dimensions of the verification coupon would then be sized to accommodate the minimum code size(s). It shall be understood that numeric values for the dimensions of the electronically readable code(s) given herein are for example purposes only, that the minimum dimensions of the electronically readable codes may change depending upon the resolution of the code reader and its corresponding ability to accurately decode the data from an electronically readable code, and that the disclosure is not limited in this respect.

Once the cleaning process is complete, verification coupon(s) 100 is removed from the cleaning machine 150. A computing device having a code reader application is used to scan and read the verification code (e.g., code 104). Computing device also scans and reads the reference code (e.g., code 106). In some examples, computing device compares the data obtained from the verification code with the data obtained from the reference code. If the data obtained from the verification code is the same as the data obtained from the reference code, this means that the soil overly was removed from the verification coupon, and the cleaning process may be verified (e.g., the cleaning cycle will receive a "Pass"). In some examples, the computing device may generate a notification for display that the cleaning process was verified and/or that the cleaning process "passed" the verification procedure. If the data decoded from the verification code is not the same as the data from the reference code, this means that the soil overlay was not entirely (or adequately) removed from the verification coupon, and the cleaning process cannot be verified as passing the cleaning verification procedure (e.g., the cleaning cycle will receive a "Fail"). In some examples, the computing device may generate a notification for display that the cleaning cycle was not verified and/or that the cleaning cycle "failed" the verification procedure.

Certain electronically readable codes, (QR codes and barcodes, for example) may include built-in error correction. In some examples, the error correction level of the electronically readable verification and reference codes may be correlated to a level of "clean"; i.e., a predefined amount of soil overlay remaining after the cleaning cycle in order for the cleaning cycle to pass the cleaning verification procedure. In other examples, the electronically readable verification and reference codes may include multiple levels of error correction. Each level of error correction may be correlated to a level of clean; i.e., the lowest level of error correction (the least amount of error correction) may correlated to "clean" and successively higher levels of error correction (relatively more error correction) correlated to successively less "clean" or one or more levels of "fail". The amount of soil overlay removed/remaining may be determined by a comparison of the data obtained from the cleaned verification code and the data obtained from the reference code, and determining which of the multiple levels of error correction is required for the verification code data to match the reference code data. This level of error correction may be correlated to a level of "clean".

In some examples, dishmachine 150 uses dish racks with electronically readable identifiers to uniquely identify each rack and to identify the types of article(s) in the rack. In the example of FIG. 3, rack 154 includes an RFID tag 180. The rack identification data stored in RFID tag 180 includes a rack type and a unique rack identifier. The rack type corresponds to the type of articles washed on or in the rack. For example, the rack type may be identified as a pot/pan rack, a glassware rack, a dishware rack, a utensil rack, etc. The rack identifier is uniquely associated with an individual rack. The rack identifier enables individual tracking of each cleaning cycle with a uniquely identified rack and associated rack type, along with a date and time stamp. Example rack identification systems are described in U.S. Pat. Nos. 7,437, 213 and 6,463,940, which are incorporated by reference herein in their entirety.

Dishmachine controller 170 includes a tag reader configured to read the RFID tag 180 and obtain the rack identification data. Dishmachine controller 170 (or other computing device) may associate the unique rack identifier with the current cleaning process. This also results in identifying the type of articles that were cleaned during the current cleaning cycle, and linking the individual rack and article type with any other data associated with the current cleaning cycle (e.g., cycle type, water volumes and temperatures, amounts/volumes/weights of chemical product dispensed, cycle times, etc.).

Dishmachine controller 170 further determines the rack type, and thus identifies the type of articles being washed during the current cleaning process. The dishmachine controller 170 may adjust the cleaning process to best address the type(s) of articles being cleaned and the type(s) of soils typically encountered when cleaning those articles. For example, as discussed above, the different types articles that are cleaned in a dishmachine may experience different types of soils. For example, pots and pans may be soiled with large amounts of starch, sugar, protein, and fatty soils. In contrast, glasses are not typically heavily soiled but have hard to remove soils like lipstick, coffee and tea stains. Once dishmachine controller 170 identifies the type of article in the rack, it can modify the dishmachine cycle in a manner that selects optimal wash/rinse cycles, times, temperatures, and chemical compositions needed to clean the articles while minimizing use of water, energy, or chemical cleaning product. For example, running a wash cycle with chemical compositions that are effective at cleaning pots and pans would likely be too much chemistry for a rack of glasses. Rack identification allows dishmachine controller 170 to use the correct type and concentration of chemistry for the article to be cleaned. And by not overusing chemistry, the dishmachine can use less chemistry overall while still achieving the expected cleaning performance results.

These RFID tags, such as tag 154, may be integrated into the dishmachine rack in many ways. They may be physically attached to the rack by use of a fastener, may be molded directly into the rack, or may be attached to the rack with a molded or machined clip or bracket. They may be located at any location on the rack, but preferably will be located along the outside edge of the rack, so they do not interfere with the spray of water that cleans the dishes. The mounting feature may allow the RFID tag to be attached to both new and pre-existing racks. One method of doing this is with an injection molded bracket that is designed to hold the RFID tag in a specific position on the rack, and can be inserted into many types of racks. In some examples, the tag is placed in a consistent location on each rack, which can be read through an antenna located mounted in, on or near floor 155 or sidewall 157 of the dishmachine. In other examples, the tag reader may be located outside of the dishmachine or on an outside wall of the dishmachine.

Identification of individual racks and rack types, and the cleaning process data that may also be obtained by the dishmachine, may further be analyzed to identify the number and type of wash processes over specified time periods, view historical data on problems encountered during the wash process, view data regarding the general operation of the machine (e.g., how many cycles per day/week/month, how often it is drained, etc.), and the type of ware washed during particular times and days of the week, in addition to cycle times, temperatures, dispensed chemical amounts, and can help create reports to improve management of a dish washing facility.

Figure 4B:
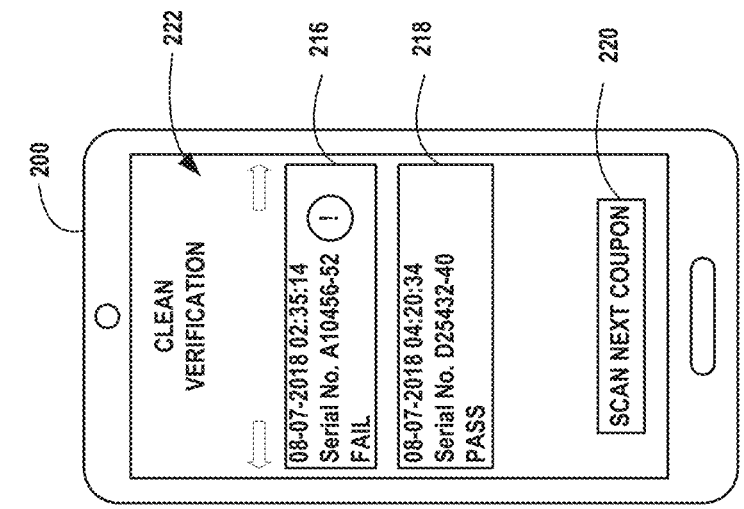
FIGS. 4A and 4B show a block diagram and a front view, respectively, of an example computing device configured to verify a cleaning process using an electronically readable cleaning process verification coupon in accordance with the present disclosure.
Figure 4A:
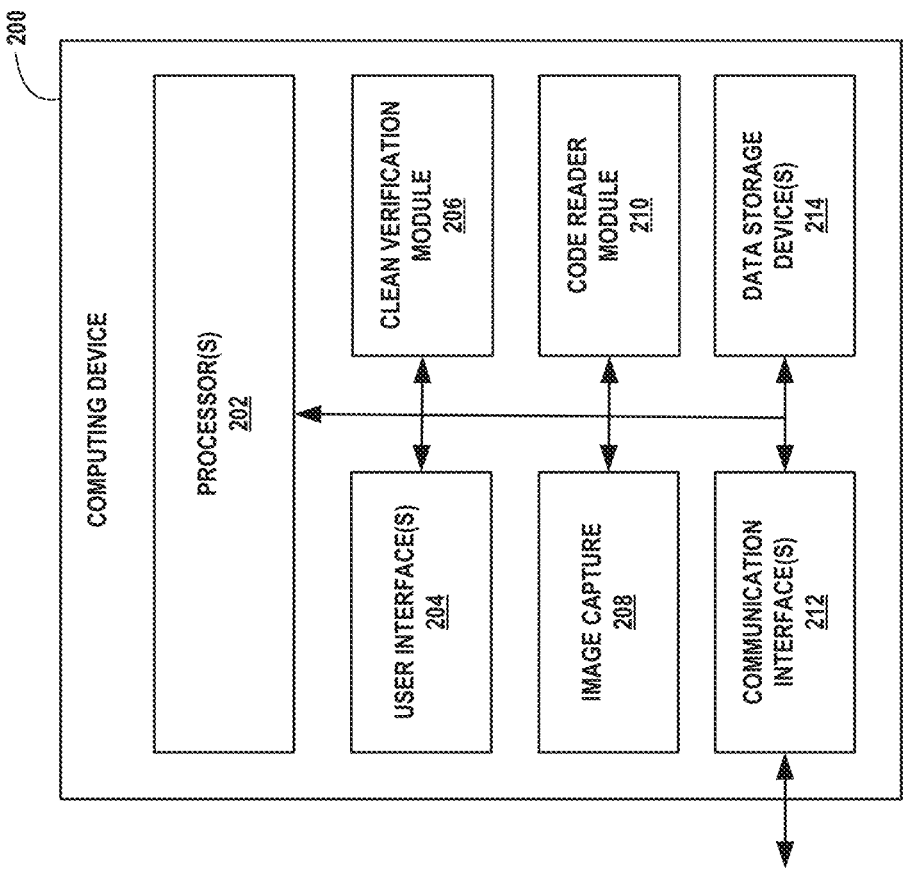

FIGS. 4A and 4B show a block diagram and a front view, respectively, of an example computing device 200 configured to verify a cleaning process using an electronically readable cleaning process verification coupon in accordance with the present disclosure. Computing device 200 may include, for example, a mobile computing device, a smart phone, a tablet computer, a laptop computer, a desktop computer, a server computer, a personal digital assistant (PDA), a portable gaming device, a portable media player, an e-book reader, a wearable computing device, a smartwatch, a television platform, or another type of computing device.

Computing device 200 includes one or more processors 202, one or more user interface components 204, one or more communication components 212, and one or more data storage components 214. User interface components may include one or more of audio interface(s), visual interface(s), and touch-based interface components, including a touch screen, display, speakers, buttons, keypad, stylus, mouse, or other mechanism that allows a person to interact with a computing device. Communication components 212 allow computing device 200 to communicate with other remote or local computing devices via wired and/or wireless connections.

Computing device 200 further includes an image capture or imaging device 208, a code reader module 210 and a clean verification module 206. Image capture device 208 may include a digital camera, a scanner, a webcam, or any other type of imaging device. Code reader module 210 and clean verification module 206 include computer readable instructions configured to be executed on the one or more processors 202. Code reader module 210 includes computer readable instructions configured to be executed on the one or more processors 202 to enable computing device 200 to scan electronically readable code(s) using image capture components 208 and to decode the data.

Clean verification module 206 includes computer readable instructions configured to be executed on the one or more processors 202 to enable computing device 200 to carry out a cleaning process verification procedure. In some examples, clean verification module 206 includes computer readable instructions configured to be executed on the one or more processors 202 to enable computing device 200 to receive and analyze the decoded data to determine whether a soil overlay was completely removed (or removed to within a specified tolerance), and to determine whether the cleaning process "passed" or "failed" the cleaning process verification procedure. In other examples, clean verification module 206 includes computer readable instructions configured to be executed on the one or more processors 202 to enable computing device 200 to communicate with a remote or server computing device to send and/or receive information associated with a clean process verification procedure.

Clean verification module 206 may further include instructions that enable processors 202 to generate one or more notifications for display on user interface 204 of computing device 200 regarding the results of the cleaning process verification procedure. For example, FIG. 4B shows computing device 200 (in this example, a smart phone or tablet computer) having a touch screen display 222. Notifications 216 and 218 are displayed on the touch screen 222. Notification 216 indicates that a cleaning process carried out on Aug. 7, 2018, using a verification coupon having Serial No. A10456-52, received a FAIL for the corresponding cleaning process verification procedure. In other words, the soil overlay on verification coupon having Serial No. A10456-52 was not completely removed. Notification 216 may include an (!) indication, for example, to help draw a user's attention to the fact that this particular cleaning process failed, and that it may need to be addressed. Notification 218 indicates that a cleaning process carried out on Aug. 7, 2018, using a verification coupon having Serial No. D25432-40, received a PASS for the corresponding cleaning process verification procedure. In other words, the soil overlay on verification coupon having Serial No. D25432-40 was completely removed.

A button 220 displayed on touchscreen 222 and labeled "Scan Next Coupon" or similar may be tapped to enable a user to scan another verification coupon. For example, tapping of button 220 by a user may cause processor(s) 202 to present a code reader on touchscreen 222 of computing device 200. The user may then use the displayed code reader to scan the electronically readable code of another verification coupon to validate the next cleaning process.

In some examples, notifications 216 and/or 218 on touch screen 222 may be tapped to cause computing device 200 to display additional information concerning that particular cleaning process verification procedure. For example, tapping notification 216 on touchscreen 222 may cause a more detailed report concerning the cleaning process carried out on Aug. 7, 2018, using a verification coupon having Serial No. A10456-52, and receiving a FAIL to be displayed on touchscreen 222. The more detailed report may include information such as the date and time of the cleaning cycle, a unique identification of the cleaning machine, a unique identification of the person running the cleaning process and/or the cleaning verification procedure, the type of articles cleaned during the cleaning process, the types of racks or trays used during the cleaning process, the type of article being cleaned during the cleaning process, the types and amounts of chemical product dispensed during each cycle of the cleaning process, the volume of water dispensed during each cycle of the cleaning process, a "pass" or "fail" indication for the cleaning process, or other information relevant to the cleaning process or the cleaning process verification procedure. The more detailed report may further include information concerning the how much of the soil overlay was removed and/or how much of the soil overlay remained. It may further include information on possible reason(s) why the cleaning process failed (e.g., whether a hardware-related or a chemistry-related failure), and/or suggested correction(s) for addressing the failure. Tapping on notification 216 on touchscreen 222 may cause processor(s) 202 to generate for display a similar detailed report concerning the cleaning process carried out on Aug. 7, 2018, using a verification coupon having Serial No. D25432-40 and receiving a PASS.

Storage components 214 of computing device 202 include data used or generated by computing device 200 during execution of the clean verification module, the code reader module, or any other functionality of computing device 202. For example, storage components 214 include any data received from image capture device 208, data entered by a user via user interface components 204, or data used or generated by code reader module 210 and/or clean verification module 206.

Figure 5:
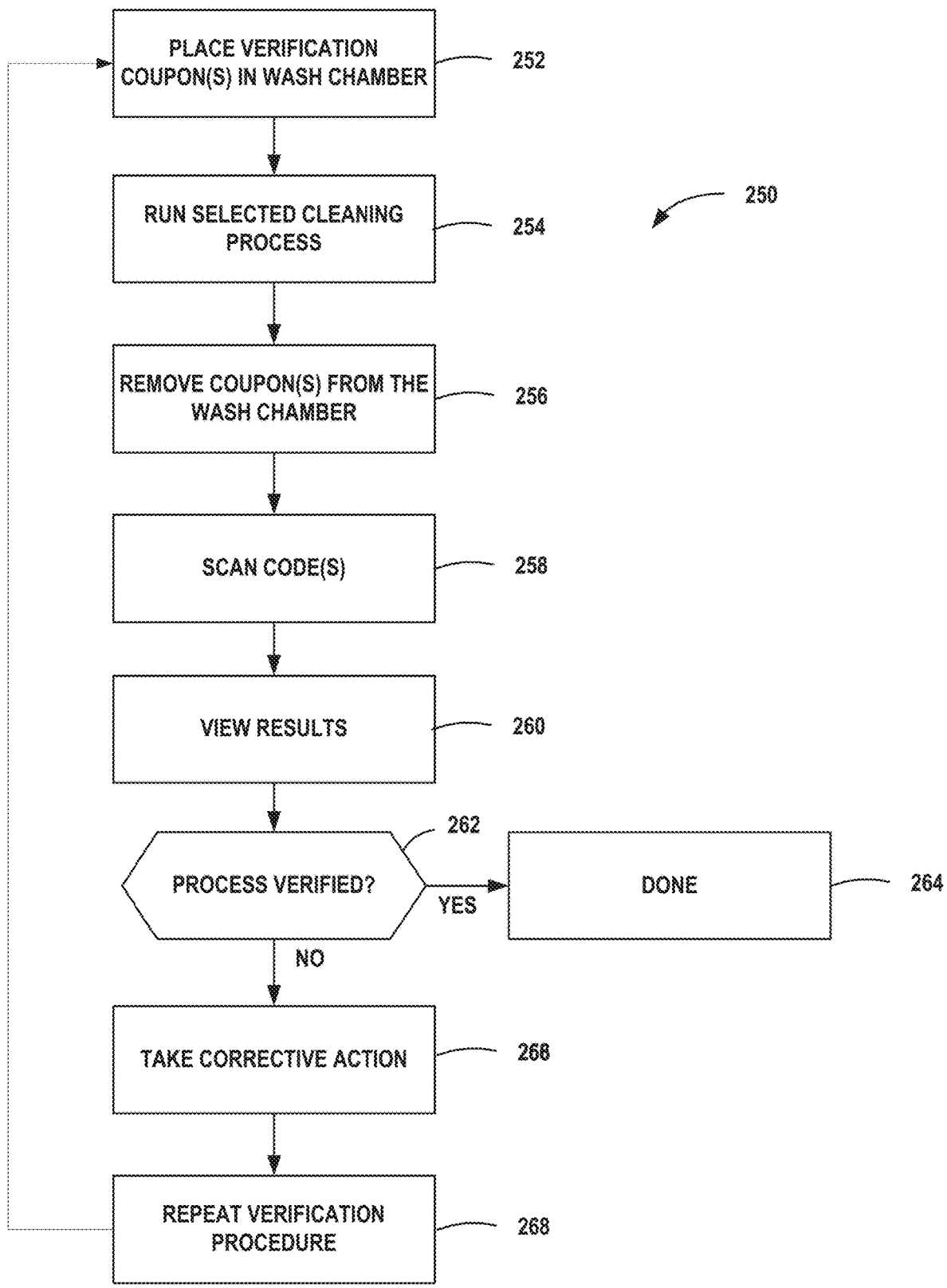
FIG. 5 is a flowchart illustrating an example process by which a cleaning process may be verified using an electronically readable cleaning process verification coupon in accordance with the present disclosure.

FIG. 5 is a flowchart illustrating an example verification procedure (250) by which a cleaning cycle or process may be verified using an electronically readable cleaning process verification coupon in accordance with the present disclosure.

A user places one or more cleaning process verification coupon(s), such as coupon(s) 100 or 120 as shown in FIGS. 1A-1B and/or 2A and 2B, in the wash chamber of an automated cleaning machine (252). In some examples, the verification procedure is conducted when the cleaning machine is otherwise empty; in other words, the verification procedure is conducted when there are no articles to be cleaned in the wash chamber of the cleaning machine. In other examples, the verification procedure is conducted when the articles to be cleaned are present in the wash chamber during the verification procedure.

The automated cleaning machine may include any type of dishwasher or warewashing machine, including commercial dishwashers, warewashers, and sanitizers, high or low temperature machines, conveyor dishwashers, door-type dishwashers, under counter dishwashers, glass washers, pot/pan/utensil washers, etc.; any type of medical cleaning equipment, including washer/decontaminators, steam sterilizers, autoclaves, ultrasonic washers, tunnel washers, cart washers, etc.; any type of laundry machines; and any other types of cleaning machine. It shall therefore be understood that the disclosure is not limited with respect to the type of automated cleaning machine or the articles to be cleaned.

Once the verification coupon(s) are placed in the wash chamber of the cleaning machine, the user initiates, or runs, the selected cleaning process (254). When the cleaning process is complete, the user removes the cleaning process verification coupon(s) from the wash chamber of the cleaning machine (256). As a result of the cleaning process, all or part of the soil overlay on the cleaning process verification coupon will have been removed, and the cleaning process is verified based on the portion of the electronically readable verification code revealed by the complete or partial removal of the soil overlay.

To verify the cleaning process (i.e., test or confirm the efficacy of the cleaning process), the user may use a code reader application or a cleaning verification application residing on a user computing device to scan the verification area (such as verification areas 102 or 122 of FIGS. 1 and 2) of the verification coupon, and thus to scan the portion (all or part) of the electronically readable code revealed by removal of the soil overlay during the cleaning process (258). The user computing device may further scan the reference area (such as reference areas 106 or 126 of FIGS. 1 and 2) of the verification coupon, and thus scan the electronically readable reference code (258).

The code reader application may include a webcam or mobile phone-based code reader application (such as a QR code or barcode reader application), a customized code reader application, a handheld scanner/terminal, a fixed mount code scanner, a presentation scanner, an in-counter scanner, or any other type of code reader/scanner. The code reader may further include a laser scanner, linear imager, 2D area imager, or any other appropriate code reader/scanning technology. The cleaning verification module/application (such as clean verification module 206 of FIG. 4A) may include code reader functionality, or may use a separate code reader module (such as code reader module 210 of FIG. 4A).

The code reader application or cleaning verification application may decode (e.g., read or attempt to read) the data encoded in the portion of the electronically readable code revealed by removal of the soil overlay during the cleaning process, and may compare the data obtained from the verification code to data obtained from the reference code. The results of the comparison, and any associated cleaning score (such as "Pass", "Fail", or other levels of clean) may be displayed on the user computing device (such as shown in FIG. 4B), and these results may be viewed by the user (260). If the computing device was able to correctly read the electronically readable verification code printed on the verification coupon, the clean verification application will determine that the soil overlay was adequately removed (removed to within a specified tolerance) and will verify the cleaning process (262). Because the cleaning process was verified, no corrective action is necessary, and the process is complete (264). If the cleaning verification application is not able to correctly read the electronically readable code, this means that the soil overlay was not adequately removed (not removed to within a specified tolerance) and the cleaning process is not verified (262). Corrective action should then be taken (268) and the cleaning verification procedure repeated (268) to determine the reason for the failure (e.g., mechanical failure, chemistry failure, user error, or combination of these) and/or address the cause of the failure to ensure that the cleaning machine is working properly or ensure adequate cleaning in subsequent cycles. For example, failures during a cleaning cycle can be a result of improper chemical cleaning agent(s), improper chemical agent concentration(s), insufficient water pressure, poor water quality, incorrect temperatures, cycle duration, operator error, mechanical failure, or other factors. In some examples, the results (260) may include one or more indications of the possible reasons for the failure that occurred and/or suggested corrective actions to diagnose and/or address the failure.

Although the example process (250) shown in FIG. 5 is described as a manual process in the sense that a user places the verification coupon(s) into the cleaning chamber of a washing machine, removes the verification coupon(s) from the cleaning machine, and initiates scanning of the verification and reference codes, it shall be understood that some or all of such process may be automated, and that the disclosure is not limited in this respect. For example, an automatic verification coupon feeder may advance verification coupon(s) into the wash chamber and, and an image capture device may automatically capture an image of the verification and/or reference area(s) of the verification coupon upon completion of the cleaning process. For example, the dishmachine controller 170 of FIG. 3 may include or interface to a code reader imaging device that automatically captures an image of the verification and/or reference area(s) of the verification coupon upon completion of the cleaning process.

Figure 6:
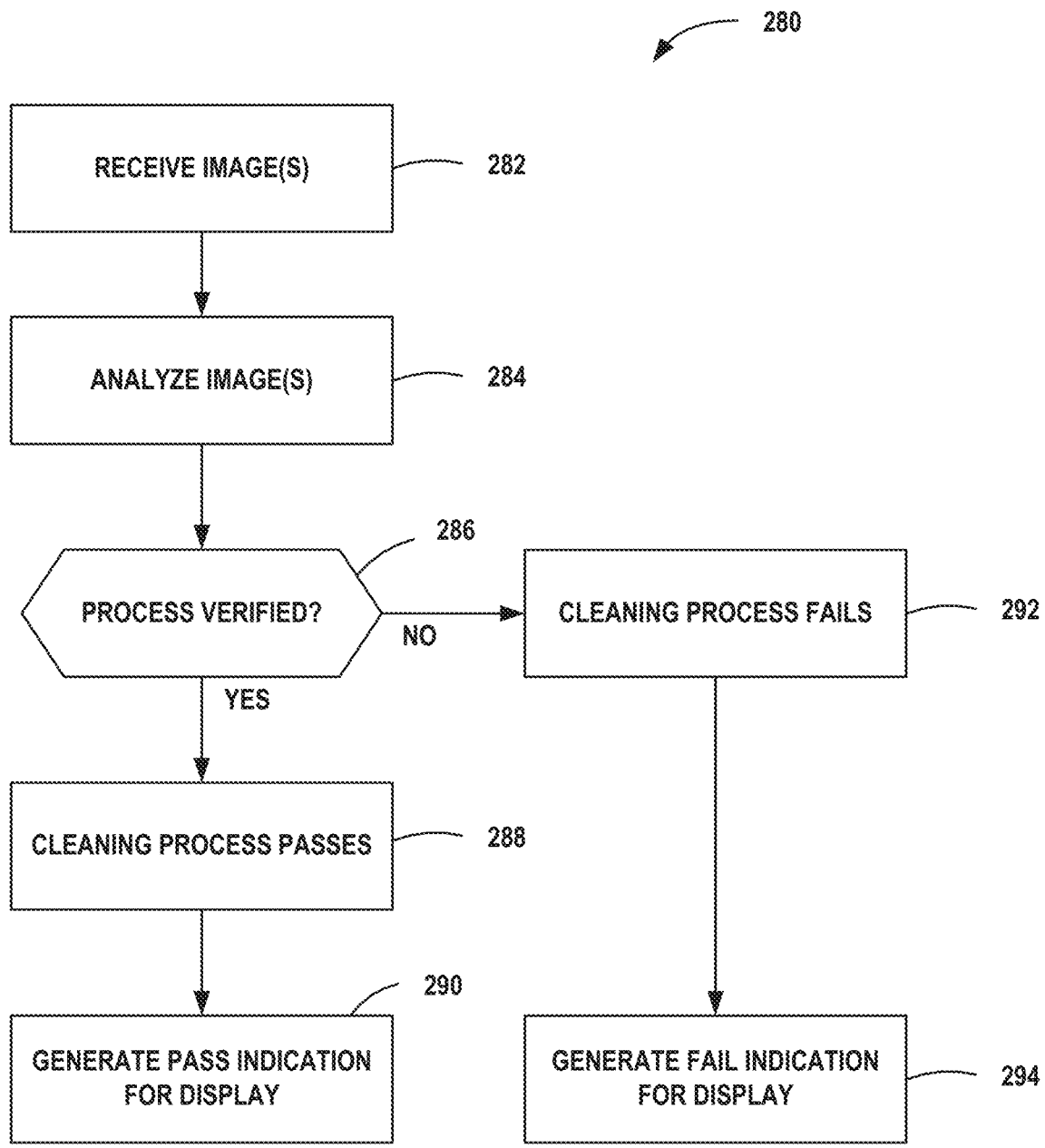
FIG. 6 is a flowchart illustrating an example process by which a computing device may verify a cleaning process using an electronically readable cleaning process verification coupon in accordance with the present disclosure.

FIG. 6 is a flowchart illustrating an example process (280) by which a computing device (such as computing device 200 as shown in FIGS. 4A and/or 4B) may verify a cleaning process using an electronically readable cleaning process verification coupon in accordance with the present disclosure. The computing device receives an image of the verification area on the cleaning process verification coupon, which will include an image of the portion of the verification code that was revealed by removal of the soil overlay during the cleaning process (282). The computing device may also receive an image of the reference area on the cleaning process verification coupon, which will include an image of the reference code printed on the verification coupon (282). The computing device analyzes the image(s) (284) to determine whether the electronically readable verification code can be read; in other words, the computing device analyzes the image(s) to determine if the data obtained from the verification code matches the data obtained from the reference code to within a specified tolerance. In some examples, the specified tolerance is expressed as a percent error correction applied to the verification code data to achieve a match with the reference code data. If the verification code is verified (e.g., the data from the verification code is within the specified tolerance of the data obtained from the reference code) (286) this means that the soil overlay was adequately removed by the cleaning process, and the computing device may verify that the cleaning process "Passes" the verification procedure (288). The computing device may then generate a "Pass" indication for display on the user interface of the computing device (290), such as shown in FIG. 4B, for example.

If during the analysis of the image (284) the data obtained from the verification code is not within the specified tolerance of the data obtained from the reference code (286), this means that the soil overlay was not adequately removed by the cleaning process. The cleaning process is not verified, and will thus "Fail" the verification procedure (292). The computing device may generate a "Fail" indication for display on the user interface of the computing device (294), such as shown in FIG. 4B, for example.

In some examples, the computing device analyzes the image (284) by comparing the data obtained from the verification code with the data obtained from the reference code. If the data obtained from the verification code is the same as the data obtained from the reference code to within a specified tolerance, this means that the soil overly was adequately removed from the verification coupon, and the cleaning process may be verified (e.g., the cleaning cycle will be marked as "Pass"). If the data decoded from the verification code is not the same as the data from the reference code to within a specified tolerance, this means that the soil overlay was not entirely removed from the verification coupon, and the cleaning process cannot be verified as passing the cleaning verification procedure (e.g., the cleaning cycle will be marked as "Fail").

In some examples, the specified tolerance is expressed as a percent error correction applied to the verification code data to achieve a match with the reference code data (that is, the minimum amount of error code applied for the verification code to scan correctly). In such examples, the computing device may analyze the image (284) and determine a minimum level of error correction at which the data obtained from the verification code matches the data obtained from the reference code. This error correction level may be correlated to a level of "clean"; i.e., a predefined amount of soil overlay removed/remaining after completion of the cleaning cycle. In such examples, analysis of the images (284) may include one or more levels of error correction. Each level of error correction may be correlated to a level of clean; i.e., the lowest level of error correction (the least amount of error correction or no error correction) may be correlated to "clean" or "pass" and successively higher levels of error correction (relatively more error correction) may be correlated to successively lower levels "clean" or one or more levels of "fail". The amount of soil overlay removed/remaining may be determined by a comparison of the data obtained from the cleaned verification code and the data obtained from the reference code, and determining which of the multiple levels of error correction must be applied to the verification code data in order for the verification code data to match the reference code data. This level of error correction may be correlated to a level of "clean".

Table 1 shows an example of multiple levels of "clean" correlated to multiple levels of error correction. The error correction levels refer to the lowest amount of error correction applied to the data obtained from the verification code to accurately reconstruct the data obtained from the reference code. The level of error correction required generally corresponds to an amount of soil overlay remaining over (obscuring) the verification code after the cleaning process. A low level of error correction means that a very small amount (or none) of the soil overlay remained after completion of the cleaning cycle, and that thus almost all of the verification code was revealed by removal of the soil overlay, and that thus a very small amount (or none) error correction was required to accurately reconstruct the data encoded on the verification code. The more soil overlay remaining, the higher level of error correction that may be required to ensure that the verification code data can be accurately reconstructed, and thus the higher the fail level.

TABLE 1

| Level of Clean | Error Correction | Description |
| --- | --- | --- |
| Pass-Clean | 0-2% | Clean process verified-cleaning cycle "Passes" the verification procedure |
| Fail-Level 1 | 6-9% | A relatively small amount of soil overlay remaining-the lowest "Fail" level indicating one or more issues with the cleaning cycle |
| Fail-Level 2 | 12-15% | A larger amount of soil overlay remaining-a higher "Fail" level indicating one or more issues with the cleaning cycle |
| Fail-Level 3 | 25-30% | A larger amount of soil over overlay remaining-a higher "Fail" level indicating more serious chemical/mechanical problems with the cleaning cycle |
| Fail-Level 4 | Unreadable | The amount of soil overlay remaining prevents reading of the verification code-the highest "Fail" level indicating more serious chemical/mechanical problems with the cleaning cycle |

It shall be understood that the levels of clean and the corresponding amount of error correction and descriptions listed in Table 2 are for example purposes only, and that the disclosure is not limited in this respect. For example, some applications may include multiple "Pass" levels, or only a single "Pass" level and a single "Fail" level. In other examples, the error correction levels corresponding to each level of "Pass" or "Fail" may be different. Likewise, the description of each "Pass" or "Fail" level may be different depending upon the application in which the clean verification procedure is implemented.

Figure 7:
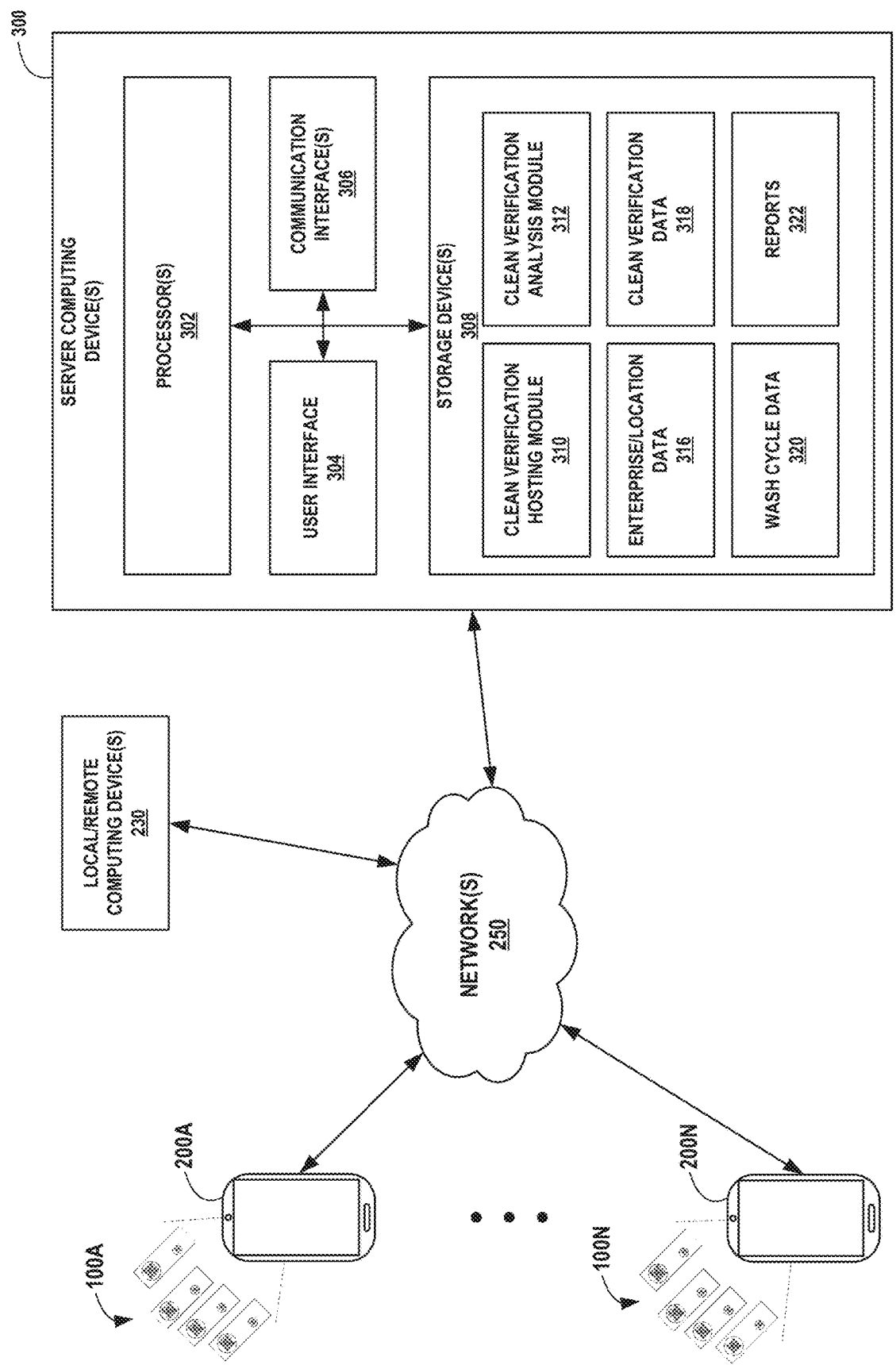
FIG. 7 is a block diagram of a computing environment that verifies cleaning processes using electronically readable cleaning process verification coupons in accordance with the present disclosure.

FIG. 7 is a block diagram of a computing system environment 301 that verifies cleaning processes using electronically readable cleaning process verification coupons in accordance with the present disclosure. System 301 includes one or more server computing device(s) 300, a plurality of user computing devices 200A-200N, and one or more local/remote computing device(s) 230.

Server computing device(s) 300 may remotely receive and analyze data associated with one or more cleaning processes collected by computing device(s) 200A-200N from scan(s) of one or more verification coupons 100A-100N. In this sense, server computing device(s) 300 may provide a so-called cloud-based service for verification of cleaning processes taking place at one or more locations or local environments associated with each of computing device(s) 200A-200N.

Server computing device(s) 300, user computing devices 200A-200N, and remote/local computing device(s) 230 communicate using one or more network(s) 250. Network(s) 250 may include, for example, one or more of a dial-up connection, a local area network (LAN), a wide area network (WAN), the internet, a wireless or Wi-Fi network, a cell phone network, satellite communication, Bluetooth, Zigbee, near field communication (NFC) and/or other means of short- or long-range electronic communication. The communication within network(s) 330 may be wired or wireless. Remote/local computing device(s) 230 may include, for example, one or more of a server computing device, a desktop computing device, a laptop computing device, a tablet computing device, a mobile computing device (such as a smart phone) a personal digital assistant, a pager, or any other type of computing device.

Each of the plurality of user computing devices 200A-200N may be used to scan a plurality of verification coupons, indicated generally by reference numerals 100A-100N, to verify a corresponding plurality of cleaning processes. In some examples, the user computing devices 200A-200N may be associated with a single enterprise, business entity or location. In other examples, some of the user computing devices 200A-200N are associated with one enterprise, business entity or location, and other of the user computing devices 200A-200N are associated with a separate, unrelated, enterprise, business entity or location. In a chain restaurant environment, for example, each of user computing devices 200A-200D may be associated with a different location of the chain restaurant, while each of user computing devices 200A-200D are associated with the same parent corporation or business enterprise. At the same time, user computing devices 200E-200N may be associated with entirely separate and unrelated locations or business entities, such as one or more different restaurants, hotels, healthcare facilities or other locations/business entities in which cleaning processes are verified using verification coupons as described herein.

Server computing device(s) 300 includes one or more processing unit(s) 302 and one or more data storage device(s) 308. Server computing device(s) 300 may further include one or more user interface components 304 and one or more communication interface components 306. The communication interface components 306 allow server computing device(s) 300 to communicate with one or more of computing device(s) 200A-200N and remote/local computing device(s) 230 via network(s) 250.

Storage device(s) 308 include a clean verification hosting module 310, a clean verification analysis module 312, enterprise/location data 316, clean verification data 318, wash cycle data 320, and reports 322.

Clean verification hosting module 310 includes computer readable instructions configured to be executed on the one or more processors 302 to enable server computing device(s) 300 to host cleaning process verification services. For example, clean verification hosting module 310 may include instructions that enable server computing device 300 to carry out one or more cleaning process verification procedures, store the results, and communicate the results to the appropriate user computing device(s) 200A-200N, or to local/remote computing device(s) 230.

Clean verification analysis module 312 includes computer readable instructions configured to be executed on the one or more processors 302 to enable server computing device(s) 300 to receive and analyze the data received from user computing devices 200A-200N to determine whether a soil overlay was removed to within a specified tolerance, and to determine whether the associated cleaning process "passed" or "failed" the cleaning process verification procedure.

Clean verification hosting module 310 may further include instructions that enable processors 202 to generate one or more notifications for display on user interface 204 of computing device 200 regarding the results of the cleaning process verification procedure. For example, the notifications 216 and 218 on touch screen display 222 in FIG. 4B may be generated remotely by server computing device(s) 300 hosting a cloud-based cleaning process verification service rather than locally by user computing device 200.

Enterprise/location data 316 may include data concerning each enterprise and/or location for which server computing device(s) 300 provides clean process verification services. For example, enterprise/location data 316 may include corporate data pertaining to an enterprise or location, location identification information, location type (e.g., restaurant, healthcare facility, etc.) types and identifiers of cleaning machines at each location, cleaning machine rack identifiers associated with each location, employee lists and identification information, data associating one or more computing devices (such as one or more of computing devise 200A-200N) with each location or enterprise, corporate and/or location cleaning process targets and tolerances, and other data related to the enterprise, the location, and/or the cleaning processes at each location.

Clean verification data 318 may include image data received from computing devices 200A-200N and any associated data, such as data entered by a user at the time of the scan, date and time stamps associated with the image data, etc. Clean verification data 318 may further include data generated by clean verification hosting module 310 or clean verification analysis module 312 during the course of performing cleaning process verification procedures. Wash cycle data 320 may include data generated for a plurality of wash cycles, in which rack identifiers are read by a tag reader associated with a cleaning machine, for example. The wash cycle data for each wash cycle may include, for example, a location identifier, a rack identifier, a rack type, a cleaning machine identifier, a date/time stamp, cycle times and lengths, water temperatures, cleaning machine settings, chemical clean product dispenser settings, times and amounts of chemical cleaning products dispensed, and any other data relevant to a wash cycle.

Clean verification hosting module 310 may link clean verification data 318 with wash cycle data 320 by comparing date/time stamps for each clean verification procedure with date/time stamps for each wash cycle (i.e., cleaning process to be verified). For example, a clean verification procedure may be matched with a cleaning process to be verified when the date/time stamp associated with the clean verification procedure is within a predetermined interval from the date/time stamp associated with the wash cycle/cleaning process. The time interval may be determined based on, for example, the cycle time/length of the overall cleaning process. For example, if the RFID tag on a rack is read at the time the rack is loaded into the wash chamber of a cleaning machine, and the verification coupon is read after completion of the cleaning cycle, the predetermined time may include at least the total cycle time for the cleaning process. In this way, the data from each wash cycle/cleaning process stored in wash cycle data 320 may be linked or associated with the corresponding clean verification results stored in clean verification data 318. This allows a user to view not only the wash cycle data corresponding to a particular wash cycle but also to view the results of the corresponding cleaning process verification procedure. The wash cycle data corresponding to each wash cycle/cleaning process may therefore be viewed, allowing a user to see a detailed report of the operating conditions of the cleaning machine for each cleaning process verification procedure. For a cleaning process receiving a "Fail", for example, a user may thus also view the corresponding operating conditions of the cleaning machine, and may thus have as much information as possible to aid in identifying the reason for the failure (e.g., mechanical, chemical, user-error, etc.), and also to identify potential corrective action to address such failures.

Clean verification hosting module 310 may also include reporting functionality by which server computing device(s) 300 may generate one or more reports concerning cleaning process verification data 318, enterprise/location data 316, and/or wash cycle data 320 for communication to and/or display by one of computing device(s) 200A-200N or local/remote computing device(s) 230. For example, tapping notification 216 on touchscreen 222 of FIG. 4B may cause a more detailed report concerning the cleaning process carried out on Aug. 7, 2018, using a verification coupon having Serial No. A10456-52, and receiving a FAIL to be generated by server computing device(s) 300 for display on touchscreen 222.

For example, the following is an example of a more detailed report concerning the cleaning process corresponding to verification coupon Serial No. A10456-52, including the cleaning process verification data and the associated wash cycle data.

Cleaning Cycle Overview

| | |
|---|---|
| Date/Time | Aug. 7, 2018 02:35:14 |
| Location | Store #302, St. Paul, MN |
| Verification Coupon | Serial No. A10456-52 |
| Clean Verification Score | FAIL |
| Coupon Type | Food Soil 3 |
| Machine Type | Single Rack/High Temperature |
| Rack Type | Dishware |
| Cycle Type | Dishware |
| Employee ID | 555-5555 |

Cleaning Cycle Details

| Parameter | Cycle Data | Specification/Target | Error | Possible Cause |
|---|---|---|---|---|
| Wash Cycle Time | 45 | 45 | | |
| Dwell Time | 8 | 8 | | |
| Rinse Time | 7 | 7 | | |
| Load Time | 5 | 5 | | |
| Total Cycle Time | 65 | 65 | | |
| Wash Water Temp. | 128° F. | 155° F. (minimum) | −27° F. (too low) | faulty temperature sensor<br>faulty heating element<br>water supply temp. too low<br>clogged inlet screen<br>supply hose blocked or kinked |
| Water Consumption | 0.47 gal/rack | 0.47 gal/rack | | |
| Sanitize/Rinse Water Temp | 145° F. | 180° F. (minimum) | −35 °F. (too low) | faulty temperature sensor<br>faulty heating element<br>water supply temp. too low<br>clogged inlet screen<br>supply hose blocked or kinked |
| Wash Product | Dishmachine Detergent-All Purpose | Dishmachine Detergent-All Purpose | | |
| Wash Product Dilution | 0.1% | 0.1% | | |
| Rinse Product | Rinse Additive-All Purpose | Rinse Additive-All Purpose | | |
| Rinse Product Dilution | 0.0020% | 0.0020% | | |
| Sanitizer Product | Solid Sanitizer | Solid Sanitizer | | |
| Sanitizer Product Dilution | 0.018% | 0.018% | | |

In this example, the water temperature for both the wash cycle and the sanitizing rinse cycle were too low (the wash water temperature for the cleaning cycle was 128° F. and the target water temperature was 155° F. minimum, and the sanitizing rinse water temperature for the cleaning cycle was 145° F. and the target sanitizing rinse water temperature was 180° F. minimum). The reason for the failure of the cleaning cycle to pass the verification procedure may therefore be because the wash cycle and sanitizing rinse water temperatures were too low. The last column of the detailed report includes possible reasons/causes for the failure and/or ways in which to address the failure.

As another example, one or more local/remote computing device(s) 230 may request reports including data corresponding to one or more specific cleaning processes, or data concerning cleaning processes at one or more specific location(s), cleaning machine(s), date(s), time(s), employee, cleaning score(s), etc. The data may be used to identify trends, areas for improvement, or otherwise assist the person(s) responsible for ensuring the efficacy of cleaning process to identify and address problems in the cleaning processes.

The report(s) may include information for one or more cleaning processes/cycles, and the data for each cleaning process may include information such as the date and time of the cleaning process, a unique identification of the cleaning machine, a unique identification of the person running the cleaning process and/or the cleaning verification procedure, the type of articles cleaned during the cleaning process, the types of racks or trays used during the cleaning process, the type of article being cleaned during the cleaning process, the types and amounts of chemical product dispensed during each cycle of the cleaning process, the volume of water dispensed during each cycle of the cleaning process, a "pass" or "fail" indication for the cleaning process, or other information relevant to the cleaning process or the cleaning process verification procedure. The report(s) may further include information concerning the how much of the soil overlay was removed and/or how much of the soil overlay remained. It may further include information on possible reason(s) why the cleaning process failed (e.g., whether a hardware-related or a chemistry-related failure), and/or suggested correction(s) for addressing the failure. The report(s) may also include information concerning the location; the business entity/enterprise; corporate clean verification targets and tolerances; cleaning scores by location, region, machine type, date/time, employee, and/or cleaning chemical types; energy costs; chemical product costs; and/or any other cleaning process data collected or generated by the system or requested by a user.

Clean verification hosting module 310 and clean verification analysis module 312 include instructions, that when executed by processor(s) 302, enable server computing device(s) to receive Clean verification hosting module 310 includes computer readable instructions configured to be executed on the one or more processors 302 to enable server computing device(s) 300 to provide cleaning process verification services and, in doing so, to carry out a plurality of cleaning process verification procedures. In some examples, clean verification hosting module 310 includes computer readable instructions configured to be executed on the one or more processors 302 to execute a process similar to the example process (280) as shown in FIG. 6.

For example, server computing device 300 may execute hosting module 310 to manage communication between server computing device(s) 300 and the one or more user computing devices 200A-200N and to execute cleaning process verification procedures between the user computing devices 200A-200N and server computing device 300. For example, server computing device 300 may receive a request for a cleaning process verification procedure and associated image data from one or more of the computing device(s) 200A-200N (282). The image data from each computing device 200A-200N may include an image of the verification area of a verification coupon and an image of the reference area of a verification coupon. Server computing device(s) 300 may analyze the image data using, for example, analysis module 312 as shown in FIG. 7 (284). Analysis module 312 may analyze the image data by decoding the data from the verification image and decoding the data from the reference image. Analysis module 312 may further compare the verification data and the reference data, and determine whether the verification data matches the reference data within a specified tolerance.

If the verification data is within the specified tolerance, the cleaning process may be verified (286). The cleaning process receives a "Pass" (288) and the server computing device may generate and transmit a pass indication for display by the associated one of the user computing devices 200A-200N. Alternatively, if the verification data is not within the specified tolerance, the cleaning process is not verified (286). The cleaning process receives a "Fail" (292) and the server computing device 300 may generate and transmit a pass indication for display by the associated one of the user computing devices 200A-200N (294).

Figure 8:
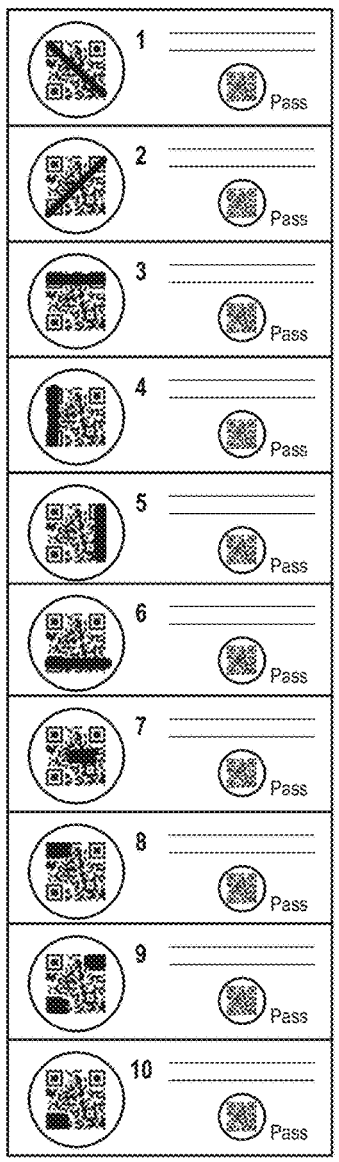
FIGS. 8 and 9 are photographs showing verification coupons 1-30 having different experimental soil patterns partially covering the electronically readable codes (QR codes and barcodes, respectively) printed thereon.
Figure 8:
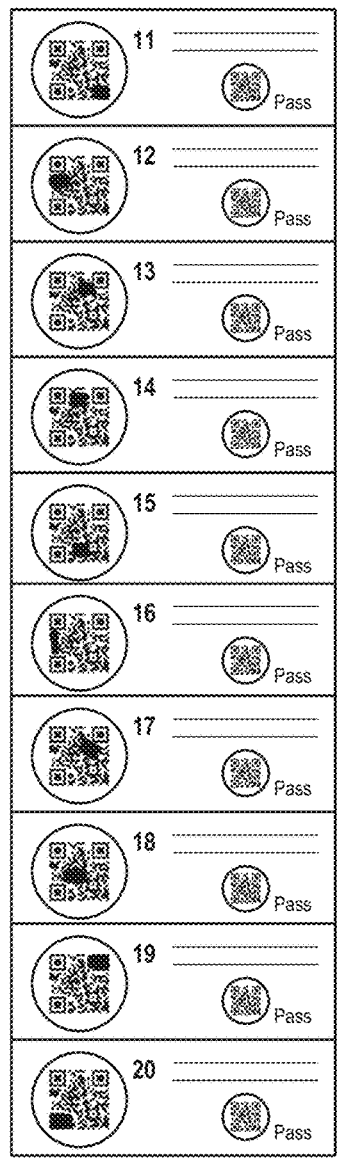
Figure 8:
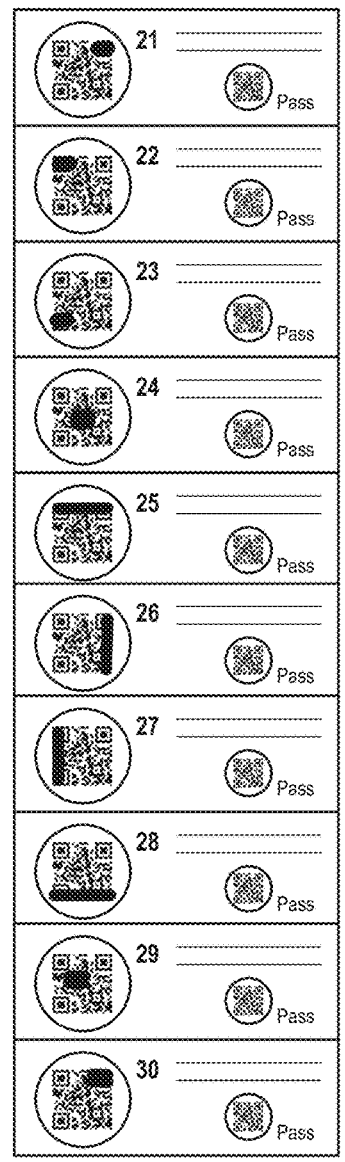

FIG. 8 is a photograph showing verification coupons 1-30 having different experimental soil patterns partially covering the electronically readable codes (in this case QR codes) printed thereon. The coupons are numbered 1-30. Each coupon includes an electronically readable code; in this example, the same QR code is printed on each coupon 1-30. An experiment was performed for purposes of determining whether the electronically readable codes covered by the different soil patterns were accurately read by a code reader application on a user computing device.

Figure 9:

Table 2 shows the results of the readability of the QR codes shown in FIG. 9. Column 1 indicates the coupon number (numbers 1-30 corresponding to the verification coupons shown in FIG. 8). Column 2 indicates whether or not the corresponding QR code was correctly read by the code reader, and column 3 indicates a Pass or Fail result of the verification procedure.

TABLE 2

| Coupon | QR Scanner Results QR Scanner Results: | |
| --- | --- | --- |
| | QR Code Read | Pass/Fail |
| 1 | No | Fail |
| 2 | No | Fail |
| 3 | No | Fail |
| 4 | No | Fail |
| 5 | No | Fail |
| 6 | No | Fail |
| 7 | Yes | Pass |
| 8 | No | Fail |
| 9 | No | Fail |
| 10 | No | Fail |
| 11 | Yes | Pass |
| 12 | Yes | Pass |
| 13 | Yes | Pass |
| 14 | Yes | Pass |
| 15 | Yes | Pass |
| 16 | Yes | Pass |
| 17 | Yes | Pass |
| 18 | Yes | Pass |
| 19 | No | Fail |
| 20 | No | Fail |
| 21 | No | Fail |
| 22 | No | Fail |
| 23 | No | Fail |
| 24 | Yes | Pass |
| 25 | No | Fail |
| 26 | No | Fail |
| 27 | No | Fail |
| 28 | Yes | Pass |
| 29 | Yes | Pass |
| 30 | No | Fail |

FIG. 9 is a photograph showing verification coupons 1-30 having different experimental soil patterns partially covering the electronically readable codes (in this case a barcode) printed thereon. The coupons are numbered 1-30. Each coupon includes an electronically readable barcode; in this example, the same barcode is printed on each coupon 1-30. An experiment was performed for purposes of determining whether the electronically readable codes covered by the different soil patterns were accurately read by a code reader.

Table 3 shows the results of the readability of the barcodes shown in FIG. 10. Column 1 indicates the coupon number (numbers 1-30 corresponding to the verification coupons shown in FIG. 9). Column 2 indicates whether or not the corresponding barcode was correctly read by the code reader, and column 3 indicates a Pass or Fail result of the verification procedure.

TABLE 3

| Coupon | Barcode Scanner Results Barcode Scanner Results: | |
| --- | --- | --- |
| | Barcode Read | Pass/Fail |
| 1 | No | Fail |
| 2 | No | Fail |
| 3 | Yes | Pass |
| 4 | No | Fail |
| 5 | No | Fail |
| 6 | Yes | Pass |
| 7 | Yes | Pass |
| 8 | No | Fail |
| 9 | No | Fail |
| 10 | Yes | Pass |
| 11 | Yes | Pass |
| 12 | Yes | Pass |
| 13 | Yes | Pass |
| 14 | Yes | Pass |
| 15 | Yes | Pass |
| 16 | No | Fail |
| 17 | Yes | Pass |
| 18 | No | Fail |
| 19 | No | Fail |
| 20 | No | Fail |
| 21 | No | Fail |
| 22 | No | Fail |
| 23 | Yes | Pass |
| 24 | Yes | Pass |
| 25 | No | Fail |
| 26 | No | Fail |

TABLE 3-continued

Barcode Scanner Results
Barcode Scanner Results:

| Coupon | Barcode Read | Pass/Fail |
|--------|--------------|-----------|
| 27 | No | Fail |
| 28 | Yes | Pass |
| 29 | No | Fail |
| 30 | Yes | Pass |

Although the examples presented herein are described with respect to automated cleaning machines for medical or food preparation/processing applications, it shall be understood that the cleaning process verification techniques described herein may be applied to a variety of other applications. Such applications may include, for example, laundry applications, agricultural applications, hospitality applications, and/or any other application in which cleaning, disinfecting, or sanitizing of articles may be useful.

In one or more examples, the functions described herein may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some examples, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Examples

Example 1: A verification coupon comprising a substrate including at least one verification area; an electronically readable verification code including encoded verification data printed within the verification area; and a soil overlay covering the verification code, the soil overlay removable by a cleaning process within an automated cleaning machine, and wherein the verification code is at least partially revealed by removal of all or part of the soil overlay during the cleaning process.

Example 2: The verification coupon of Example 1 wherein the cleaning process is verified if the encoded verification data can be correctly decoded after completion of the cleaning process.

Example 3: The verification coupon of Example 1 wherein the soil overlay includes one of a food-based soil or a medical soil.

Example 4: The verification coupon of Example 1 wherein the electronically readable code includes at least one of a Quick Response Code (QR Code), a Data Matrix or other two-dimensional barcode, a Universal Product Code (UPC), an International or European Article Number (EAN), an International Standard Book Number (ISBN), a Shipping Container Code (SCC), a Code-128 barcode, and a Code-39 barcode.

Example 5: The verification coupon of Example 1 wherein the verification coupon is mounted on a wall inside a wash chamber of the automated cleaning machine during the cleaning process.

Example 6: The verification coupon of Example 1 wherein the verification coupon is positioned on a rack that is placed inside the wash chamber during the cleaning process.

Example 7: The verification coupon of Example 1, wherein the substrate further includes a reference area, and wherein the verification coupon further comprises: an electronically readable reference code including encoded reference data printed within the reference area, wherein the encoded reference data matches the encoded verification data; and wherein the cleaning process is verified if data decoded from an image of the verification code after completion of the cleaning process matches data decoded from an image of the reference code.

Example 8: The verification coupon of Example 1 wherein the cleaning process is verified if data decoded from the image of the verification code after completion of the cleaning process may be reconstructed to match data decoded from an image of the reference code within a specified tolerance.

Example 9: A verification system comprising: a plurality of verification coupons, each verification coupon including a substrate defining at least one verification area and having an electronically readable verification code printed within the verification area, each verification coupon further including a soil overlay covering the verification code, and wherein verification code is at least partially exposed by removal of all or part of the soil overlay during a cleaning process of an automated cleaning machine; and at least one processor configured to analyze an image of the verification area of at least one of the plurality of verification coupons after completion of the cleaning process, decode the verification code from the image of the verification area, and to generate, for display on a user interface of a user computing device, a notification indicating whether or not the cleaning process has been verified based on the analysis.

Example 10: The system of Example 9 wherein the automated cleaning machine includes a dishwasher.

Example 11: The system of Example 9 wherein the articles to be cleaned include food processing, eating, or preparation articles.

Example 12: The system of Example 9 wherein the automated cleaning machine includes one of a washer/decontaminator, a steam sterilizer, an autoclave, an ultrasonic washer, a tunnel washer, or a cart washer.

Example 13: The system of Example 9 wherein the articles to be cleaned include at least one of a surgical instrument or a medical device.

Example 14: The system of Example 9 wherein the soil overlay includes at least one of a food-based soil, an organic soil, or an inorganic soil.

Example 15: The system of Example 9 further comprising a server computing device remotely located from the user computing device, and wherein the server computing device includes the at least one processor.

Example 16: The system of Example 9 wherein the user computing device includes the at least one processor.

Example 17: A method comprising running a cleaning process in an automated cleaning machine with a verification coupon present in a wash chamber of the automated cleaning machine, the verification coupon including a verification area and having an electronically readable verification code printed within a verification area and a soil overlay covering the verification code, and at least a portion of the verification code is revealed by removal of all or part of the soil overlay during the cleaning process; capturing a digital image of the verification area after completion of the cleaning process; analyzing the image of the verification area to decode the portion of the verification code revealed by removal of all or part of the soil overlay during the cleaning process; and generating, for display on a user interface of a user computing device, a notification indicating whether or not the cleaning process has been verified based on the analysis.

Example 18: The method of Example 17 further comprising verifying the cleaning process if data decoded from the portion of the verification code revealed by removal of all or part of the soil overlay matches data decoded from a reference code.

Example 19: The method of Example 17 further comprising generating a notification indicating that the cleaning process passed the verification procedure if data decoded from the portion of the verification code revealed by removal of all or part of the soil overlay matches data decoded from a reference code.

Example 20: The method of Example 17 further comprising generating a notification indicating that the cleaning process failed the verification procedure if data decoded from the portion of the verification code revealed by removal of all or part of the soil overlay does not match data decoded from a reference code.

Example 21: The method of Example 17 wherein analyzing the image of the verification area further comprises applying a first level of error correction to data decoded from the portion of the verification code revealed by removal of all or part of the soil overlay; and verifying the cleaning process if data decoded from the portion of the verification code revealed by removal of all or part of the soil overlay matches data decoded from a reference code when the first level of error correction is applied.

Example 22: The method of Example 21 further comprising generating a notification, for display on a user computing device, indicating a first failure level for the cleaning process if the data decoded from the portion of the verification code revealed by removal of all or part of the soil overlay does not match data decoded from a reference code when the first level of error correction is applied.

Example 23: The method of Example 22 wherein the notification includes possible reasons for incomplete removal of the soil overlay or corrective action that may be taken to address the incomplete removal of the soil overlay.

Example 24: The method of Example 23 wherein possible reasons for incomplete removal of the soil overlay include at least one of a mechanical failure, a chemistry failure, or a user error.

Example 25: The method of Example 22 further comprising analyzing the image of the verification area to decode the portion of the verification code revealed by removal of all or part of the soil overlay during the cleaning process and obtain therefrom a serial number uniquely identifying the verification coupon; and determining whether the uniquely identified verification coupon has been used to verify a previous cleaning process based on the serial number.

Example 26: The method of Example 25 further comprising generating, for display on a user computing device, generating, for display on a user interface of the user computing device, a notification indicating that the uniquely identified verification coupon has been used to verify the previous cleaning process if the serial number is associated with the previous cleaning process.

Various examples have been described. These and other examples are within the scope of the following claims.

The invention claimed is:

1. A method comprising:
obtaining, by one or more processors, verification code data from an electronically readable verification code that has been subjected to a performance of a cleaning process configured to at least partially remove a soil overlay initially covering the electronically readable verification code;
obtaining, by the one or more processors, reference code data from an electronically readable reference code; and
scoring, by the one or more processors, the performance of the cleaning process based on the verification code data and the reference code data.

2. The method of claim 1, wherein at least one of the electronically readable verification code or the electronically readable reference code encodes information including at least one of: a soil type or a Uniform Resource Locator (URL).

3. The method of claim 1, wherein the electronically readable verification code and the electronically readable reference code are identical.

4. The method of claim 1, wherein scoring the performance of the cleaning process comprises scoring the performance of the cleaning process based on at least one of an amount of the verification code data or content of the verification code data that can be accurately obtained from the electronically readable verification code.

5. The method of claim 1, wherein scoring the performance of the cleaning process comprises associating a passing score or a failing score with the performance of the cleaning process depending on whether the verification code data matches the reference code data.

6. The method of claim 1, wherein:
a coupon subjected to the performance of the cleaning process includes the electronically readable verification code and the electronically readable reference code; and
obtaining the verification code data and obtaining the reference code data comprises scanning the coupon.

7. The method of claim 1, wherein:
the method further comprises applying an error correction process to the verification code data to correct the verification code data so that the verification code data matches the reference code data; and
determining a score for the performance of the cleaning process based on a level of error correction needed to be performed by the error correction process to correct the verification code data so that the verification code data matches the reference code data.

8. The method of claim 1, wherein:
scoring the performance of the cleaning process comprises determining, by the one or more processors, a score for the cleaning process based on the verification code data and the reference code data, and
the method further comprises taking a corrective action based on the score indicating the cleaning process failed.

9. A system comprising:
a memory; and
one or more processors coupled to the memory and configured to:
obtain verification code data from an electronically readable verification code that has been subjected to a performance of a cleaning process configured to at least partially remove a soil overlay initially covering the electronically readable verification code;
obtain reference code data from an electronically readable reference code; and
score the performance of the cleaning process based on the verification code data and the reference code data.

10. The system of claim 9, wherein at least one of the electronically readable verification code or the electronically readable reference code encodes information including at least one of: a soil type or a Uniform Resource Locator (URL).

11. The system of claim 9, wherein the electronically readable verification code and the electronically readable reference code are identical.

12. The system of claim 9, wherein the one or more processors are configured to score the performance of the cleaning process based on at least one of an amount of the verification code data or content of the verification code data that can be accurately obtained from the verification code.

13. The system of claim 9, wherein the one or more processors are configured to, as part of scoring the performance of the cleaning process, associate a passing score or a failing score with the performance of the cleaning process depending on whether the verification code data matches the reference code data.

14. The system of claim 9, wherein:
a coupon subjected to the performance of the cleaning process includes the electronically readable verification code and the electronically readable reference code; and
the system comprises a computing device configured to scan the coupon as part of obtaining the verification code data and obtaining the reference code data.

15. The system of claim 9, wherein:
the one or more processors are further configured to apply an error correction process to the verification code data to correct the verification code data so that the verification code data matches the reference code data; and
the one or more processors are further configured to determine a score for the performance of the cleaning process based on a level of error correction needed to be performed by the error correction process to correct the verification code data so that the verification code data matches the reference code data.

16. The system of claim 9, wherein:
the one or more processors are configured to, as part of scoring the performance of the cleaning process, determine a score for the cleaning process based on the verification code data and the reference code data, and
the one or more processors are further configured to take a corrective action based on the score corresponding to indicating the cleaning process failed.

17. A method comprising:
obtaining verification code data from an electronically readable verification code that has been subjected to a performance of a cleaning process configured to at least partially remove a soil overlay initially covering the electronically readable verification code;
applying an error correction process to the verification code data to correct the verification code data so that the verification code data matches reference code data; and
determining a score for the performance of the cleaning process based on a level of error correction needed to correct the verification code data so that the verification code data matches the reference code data.

18. The method of claim 17, wherein determining the score comprises determining the score as a percent error correction applied to the verification code data to achieve a match with the reference code data.

\* \* \* \* \*